(12) United States Patent
Kamemizu

(10) Patent No.: US 6,652,550 B1
(45) Date of Patent: *Nov. 25, 2003

(54) TONGUE CLEANING DEVICE

(75) Inventor: Tadashige Kamemizu, Hyogo (JP)

(73) Assignee: Dent Care Co., Ltd., Neyagawa (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 328 days.

(21) Appl. No.: 09/609,693

(22) Filed: Jul. 6, 2000

(30) Foreign Application Priority Data

Jul. 23, 1999 (JP) .......................... 11-208695

(51) Int. Cl.[7] .............................. A61B 17/24
(52) U.S. Cl. ....................... 606/161; 15/206
(58) Field of Search ............... 15/111, 104.2, 15/27, 206; 606/161, 162; 600/569

(56) References Cited

U.S. PATENT DOCUMENTS

| | | | | |
|---|---|---|---|---|
| 758,764 A | * | 5/1904 | MacLeod ................. 15/143.1 |
| 1,861,179 A | * | 5/1932 | Gray ........................ 15/248.2 |
| D166,427 S | * | 4/1952 | Strock ........................ 15/27 |
| 2,691,182 A | * | 10/1954 | Baize ........................ 15/27 |
| D330,287 S | * | 10/1992 | Wise ........................ 15/27 |
| 5,355,547 A | * | 10/1994 | Fitjer ........................ 15/206 |
| 5,630,244 A | * | 5/1997 | Chang ...................... 15/143.1 |
| 5,954,064 A | * | 9/1999 | Motherhead ............... 132/150 |
| 6,343,396 B1 | * | 2/2002 | Simovitz et al. ........... 15/167.2 |
| 6,389,634 B1 | * | 5/2002 | Devlin et al. .............. 15/110 |

* cited by examiner

Primary Examiner—David O. Reip
(74) Attorney, Agent, or Firm—Armstrong, Westerman & Hattori, LLP

(57) ABSTRACT

The present invention provides a tongue cleaning device suitable for cleaning the tongue of those who need a caretaker, such as demented aged persons or immobile aged persons, whereby the tongue plaque scraped from the tongue dorsum is retained, the scraped tongue plaque does not drop into the oral cavity, and an injury of the lingual mucosa is prevented. To accomplish the above, both ends of an outwardly curved brush for scraping the tongue plaque on the tongue dorsum are attached to both sides of the head of a grip handle, and a spoon-shaped cover is formed at the end of the grip handle, covering the inner side of the brush in order to retain the tongue plaque scraped by the brush.

5 Claims, 5 Drawing Sheets

TONGUE CLEANING DEVICE

BACKGROUND OF THE INVENTION

The present invention relates a tongue cleaning device for scraping the tongue plaque, in particular, a tongue cleaning device suitable for a care-taker to clean the tongue of those who need a care, such as demented aged persons or immobile aged persons.

The tongue plaque, which accumulates on the tongue dorsum, consists of clusters of desquamated epithelial cells, blood cells and oral bacteria. Due to a large area of the tongue, the tongue plaque is considered to contain a larger number of bacteria than the dental plaque. It causes halitosis, and provides the sources of denture plaque or dental plaque. It has been reported that removal of the tongue plaque not only eliminates the halitosis but also prevents the denture candidiasis or dental caries.

Conventional tongue cleaning devices may be classified into two types; spatula-type devices which are used for scraping the tongue dorsum with the edge of a band-shaped or plate-shaped frame, and brush-type devices.

The spatula-type devices are further classified into rigid type devices wherein the spatula is made of metal or plastic, and soft type devices wherein the spatula is made of silicone rubber.

The brush-type devices include those on which bristles are planted like a toothbrush and those in which two twisted wires arranging a number of bristles are stretched between both sides of the Y-shaped frame body.

Said conventional spatula-type devices made of rigid plastic may injure the lingual mucosa and the taste buds in the lingual papillae when repeatedly applied with a strong pressure to scrape the tongue dorsum.

If the edge of the frame which comes in contact with the tongue dorsum is rounded off in order to prevent such injury, the device only slips on the surface of the tongue dorsum and cleaning of the space between the lingual papillae (lingual folds) becomes difficult.

The edge of the spatula of a soft type device whose spatula is made of silicone rubber also becomes rounded due to its deformation when pressed with a force, and cleaning of the fine space between the lingual papillae becomes difficult. In addition, the scraping function becomes weaker due to its softness.

The brush-type device on which bristles are planted like a toothbrush allows the scraped tongue plaque to fall through both sides of the device into the oral cavity, increasing the risk of accidental swallowing of the tongue plaque for the immobile aged persons.

The elasticity produced by the bristles of the brush alone may cause a strong friction force to be applied on the surface of the tongue dorsum due to short length of the bristles, increasing the risk of injury of the lingual mucosa. Furthermore, the area in which the bristles are planted tends to be large, which induces a greater gagging reflex.

The device which has bristle-planted wires stretched between both sides of the Y-shaped frame body may allow the scraped tongue plaque to overflow through the upper side of the brush, similarly increasing the risk of accidental swallowing of the tongue plaque for the immobile aged persons.

Although the most frequent cause of death among the aged persons is reported to be acute pneumonia, an epidemiological examination conducted at the special-care homes for the aged persons reveals that the unidentified fever frequently observed in the immobile aged persons is attributable to aspiration pneumonia caused by indigenous bacteria in the oral cavity.

Furthermore, reduced salivation is known as one of the oral phenomena of the aged persons. Self-cleaning efficiency of saliva in the oral cavity is thereby reduced, allowing accumulation of the tongue plaque and causing so-called senile halitosis.

In addition, the immobile aged persons tend to consume liquid diet, which reduces the mechanical self-cleaning efficiency associated with consumption of fibrous diet. This, coupled with reduced salivation, makes the oral environment more favorable for the tongue plaque and food debris to accumulate.

Furthermore, the immobile aged persons who have little resistance to diseases tend to have reduced cough reflex function or dysphagia, and therefore food debris or indigenous bacteria in the oral cavity which normally do not infect healthy people who have much resistance to diseases may accidentally enter into the lungs while asleep, and may cause inapparent pneumonia, occasionally leading to the death of immobile aged persons.

In order to prevent this, so-called oral care such as cleaning of teeth, treatment of alveolar pyorrhoea and removal of the tongue plaque are demanded in addition to removal of food debris attached to the denture and cleaning of the denture itself.

Among these, removal of the tongue plaque by cleaning the tongue dorsum has often been neglected. It has been neglected because it was pointed out in the past that the risk of injuring the lingual mucosa and the taste buds in the lingual papillae and the incidence of subsequent chronic inflammation would increase if the tongue dorsum is scrubbed with an excessive pressure. The use of whale whiskers or bamboo spatula was therefore refrained and cleaning of the tongue was discouraged.

As mentioned above, aged persons have a tendency to accumulate the tongue plaque due to reduced salivation. Moreover, the tongue dorsum tends to be dry and the lingual mucosa is fragile in these persons. Therefore even a weak force may injure the lingual mucosa.

Especially when a care-taker cleans the tongue of those who need a care, such as demented aged persons or immobile aged persons, it is not possible for the care-taker to adjust the intensity of scraping to the pain sensation of the patient. Therefore, there is a risk of accidental injury of the lingual mucosa of the patient by scraping the tongue dorsum too strongly being unaware of the pain of the patient. The tongue cleaning device a therefore requires considerations for prevention of injury of lingual mucosa caused by scraping the tongue dorsum with an excessive pressure.

All the conventional tongue cleaning devices have been designed for healthy people to clean their own tongue by themselves in order to remove their own halitosis. Since the users can adjust the applying pressure by themselves, the device has no pressure-reducing function against an excessive pressure.

Furthermore, there have been no considerations to completely prevent spilling of the scraped tongue plaque in the oral cavity, which may cause aspiration pneumonia in the immobile aged persons who have decreased resistance to diseases.

BRIEF SUMMARY OF THE INVENTION

The present invention, in consideration of the foregoing, provides a tongue cleaning device which retains the tongue plaque scraped from the tongue dorsum prevents the scraped tongue plaque from dropping into the oral cavity, and prevents injury of the lingual mucosa, and is therefore suitable for cleaning the tongue of those who need a care, such as demented aged persons or immobile aged persons.

In order to solve the above-mentioned problem, the tongue cleaning device provided in the present invention comprises an outwardly curved brush both ends of which are attached to both sides of the head of a grip handle for scraping the tongue plaque on the tongue dorsum, and a spoon-shaped cover formed at the end of said grip handle covering the inner side of said brush in order to retain the tongue plaque scraped by said brush.

In the tongue cleaning device with above-mentioned construction, an outwardly curved brush is placed at the end of a grip handle, and a spoon-shaped cover is formed covering the inner side of the brush, and therefore the tongue plaque scraped from the tongue dorsum is retained inside the outwardly curved brush and in the cover, and the scraped tongue plaque does not drop into the oral cavity, thereby preventing accidental swallowing of the tongue plaque in those who need a care, such as demented aged persons or immobile aged persons.

Furthermore, by using an outwardly curved brush wherein a number of bristles are spirally arranged between the two twisted wires, the contact pressure onto the tongue dorsum is reduced by the elasticity of the outwardly curved wires so that the lingual mucosa may not be injured. Moreover, the cover serves as a stopper of the brush in order to prevent excessive deformation of the brush, as excessive deformation of the brush may reduce the scraping efficiency.

The tongue cleaning device in accordance with the present invention preferably comprises a spoon-shaped cover integrally formed at the end of a grip handle with the concave side facing below, a brush for scraping the tongue plaque on the tongue dorsum formed by arranging a number of bristles spirally between the two twisted wires, wherein said brush is placed under said cover so that said wires of said outwardly curved brush are covered by said cover and both ends of the wires of said brush are attached to both sides of the under side of said cover, whereby the tongue plaque scraped by said brush is retained in said cover preventing said tongue plaque from overflowing through the upper side of said brush, and excessive deformation of said brush due to contact pressure of said brush applied onto said tongue dorsum is inhibited by said cover.

The tongue cleaning device with above-mentioned construction has a spoon-shaped cover formed integrally at the end of a grip handle and an outwardly curved brush placed under the concave part of this cover. When the brush comes in contact with the tongue dorsum and the tongue plaque is scraped, the tongue plaque scraped from the tongue dorsum is retained in the cover without overflowing through the upper side of the brush, thereby preventing the scraped tongue plaque from dropping into the oral cavity and causing accidental swallowing of the tongue plaque in those who need a care, such as demented aged persons or immobile aged persons.

The brush is formed by arranging a number of bristles spirally between the two twisted wires, and the elasticity of the outwardly curved wires reduces the contact pressure of the brush on the tongue dorsum, preventing the injury of the lingual mucosa. Excessive deformation of the brush caused by said contact pressure may reduce the scraping efficiency, but the outwardly curved wires are covered by the cover which serves as a stopper of the brush, thereby preventing excessive deformation of the brush caused by said contact pressure.

Then, making a small gap between the edge of the cover and the upper side of the brush is preferred.

By making a small gap between the edge of the cover and the upper side of the brush, additional elasticity is provided to the brush, thereby reducing said contact pressure. When the brush comes in contact with the tongue dorsum, the upper side of the brush comes in contact with the under side of the cover edge and thus the scraped tongue plaque does not overflow through the upper side of the brush.

Furthermore, forming an elastic part between the middle part and the head of the grip handle is preferred in order to reduce the contact pressure onto the tongue dorsum.

By forming an elastic part between the middle part and the head of the grip handle, three-step buffer is formed by the bristles of the brush, the wires and the elastic part, and the contact pressure onto the tongue dorsum is further reduced. Even if the care-taker scrapes with unconsciously strong pressure onto the tongue dorsum of those who receive the care, application of excessive contact pressure directly onto the tongue dorsum is thus prevented by the elasticity of the elastic part.

DETAILED DESCRIPTION OF THE INVENTION

Figure 1A:
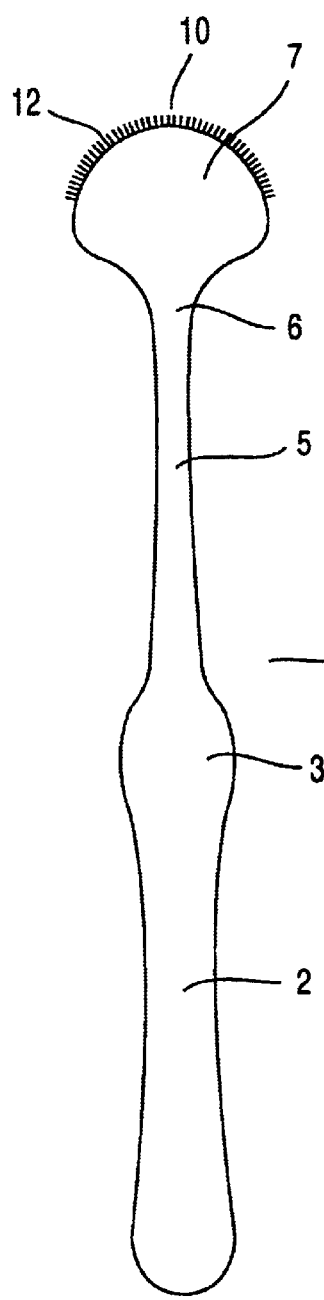
FIG. 1 illustrates a plane view (A), a bottom view (B) and a left-side view (C) of an embodiment of the present invention.
Figure 1B:
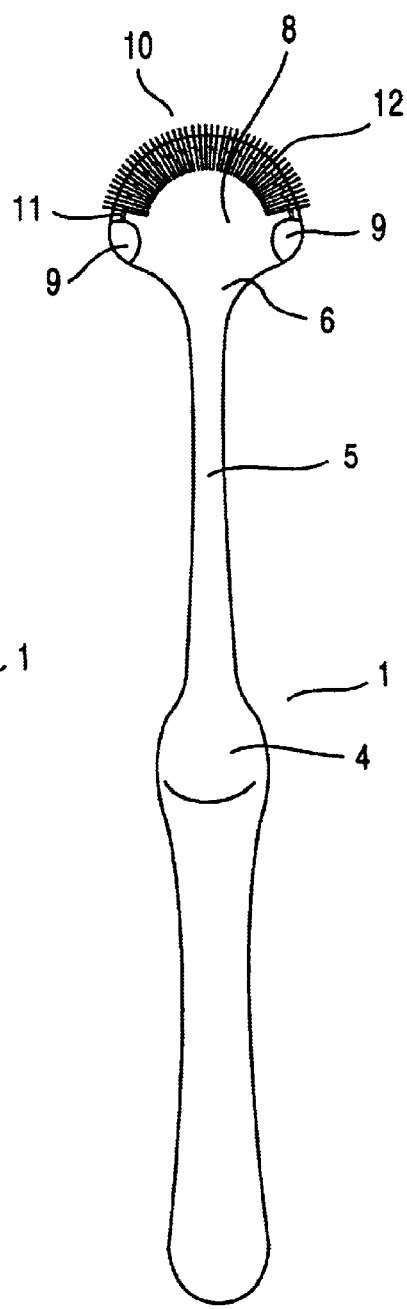
Figure 1C:
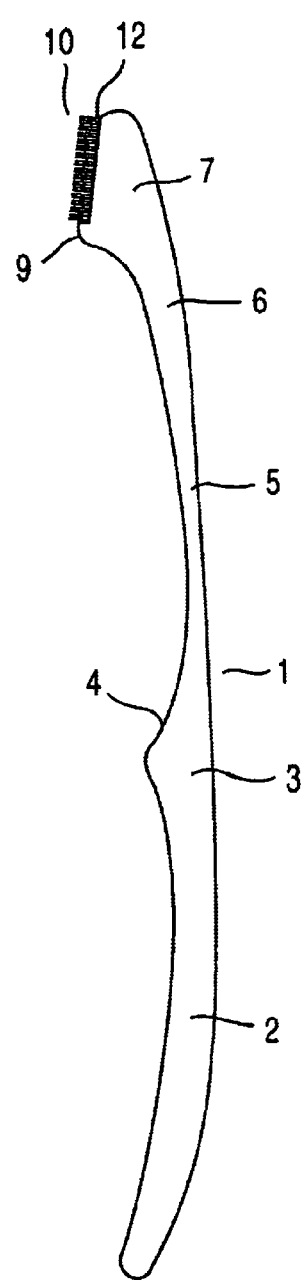
Figure 2A:
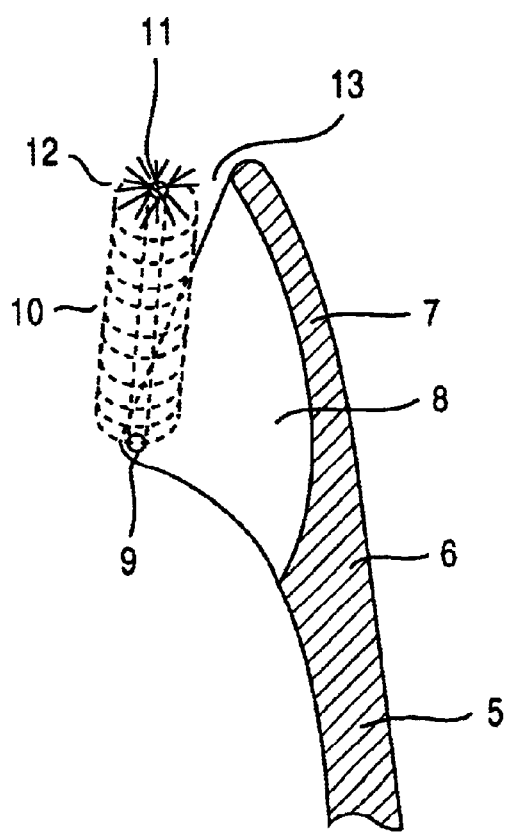
FIG. 2A is a section view of a part of FIG 1C.
Figure 2B:
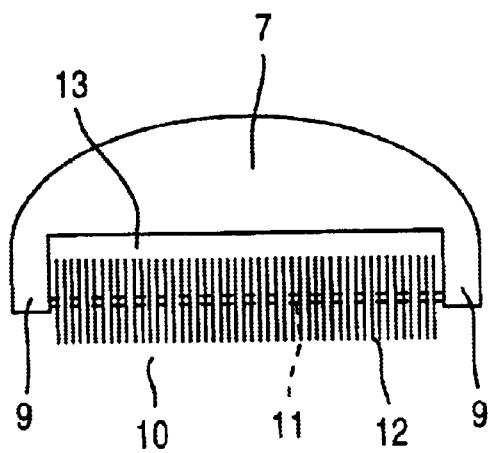
FIG. 2B shows a rear view if the object of FIG. 1A.
Figure 3:
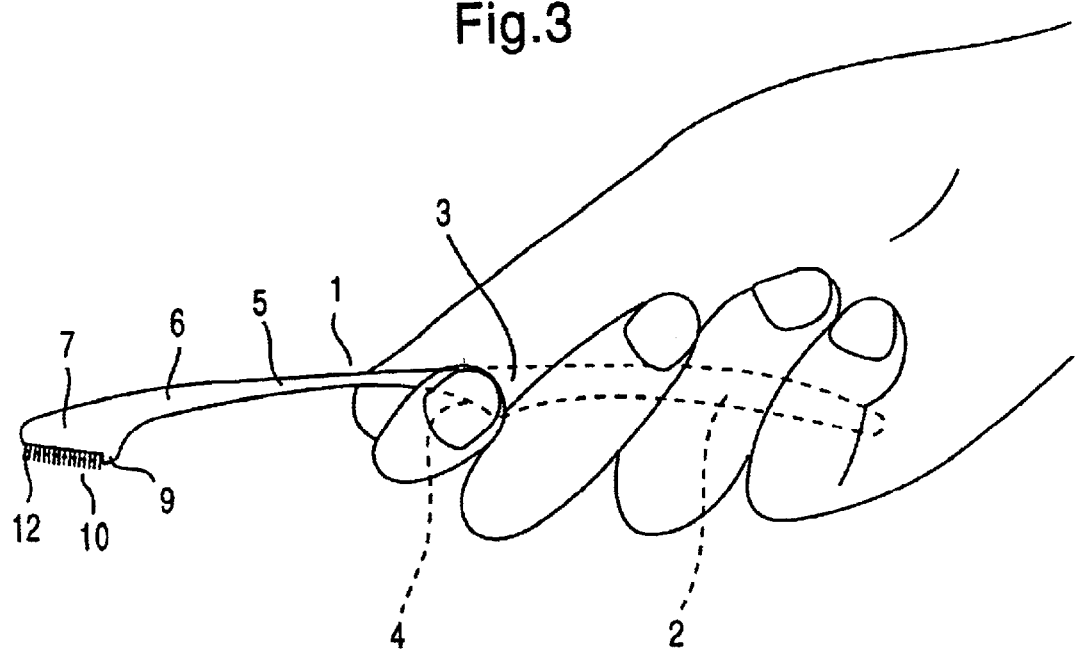
FIG. 3 is a side view of FIG. 1 in actual use condition.

The following description will discuss one embodiment of the tongue cleaning device in the present invention with reference to FIGS. 1–3. The device has a long grip handle 1 and a grip part 2. The area extending from the middle part 3 to the basal part of the grip handle 1 is formed thicker. A projection 4 is formed under the lower surface of the middle part 3 in order to fix the forefinger. A thin elastic part 5 is formed between the middle part 3 and the head 6.

A cover 7 is formed integrally at the end of the grip handle 1, which is also the end of the elastic part 5. The cover is spoon-shaped like a shell having a concave part 8 under the lower surface thereof. Protrusions 9 are formed on both sides under the lower surface of the cover 7.

An outwardly curved brush 10 is made of a number of bristles 12 having tips 12c, which are arranged between the two parallel wires 11, such as metal wires, and the bristles 12 are arranged spirally between the two twisted wires and both ends of the wires 11 of the brush 10 are implanted in the protrusions 9, attached on the cover 7. The cover 7 covers the space inside of the brush 10 and the outwardly curved wires 11, and a small gap 13 is formed between the edge of the cover 7 and the upper side of the brush 10.

When scraping the tongue plaque on the tongue dorsum of those who need a care, the tongue cleaning device is gripped with the forefinger of the care-taker positioned at the projection 4, the thumb positioned on the upper surface of the middle part 3 and the second, third and little fingers attached on the lower surface of the grip part 2. The brush 10 is put on the tongue dorsum, the grip 2 is pulled towards the operator, and the tongue plaque is thereby scraped by the brush 10.

The tongue plaque scraped from the tongue dorsum is completely retained inside the outwardly curved brush 10 and in the concave part 8 of the cover 7, and the scraped tongue plaque will never drop into the oral cavity.

Since sufficient buffer is formed by the bristles 12 of the brush 10, the wires 11 and the elastic part 5 of the grip handle 1, the contact pressure onto the tongue dorsum is reduced, and the injury of the tongue dorsum is prevented.

Furthermore, the cover 7 which covers the wires 11 of the brush 10 prevents excessive deformation of the brush 10 as the stopper and prevents reduction of scraping efficiency.

Figure 4A:
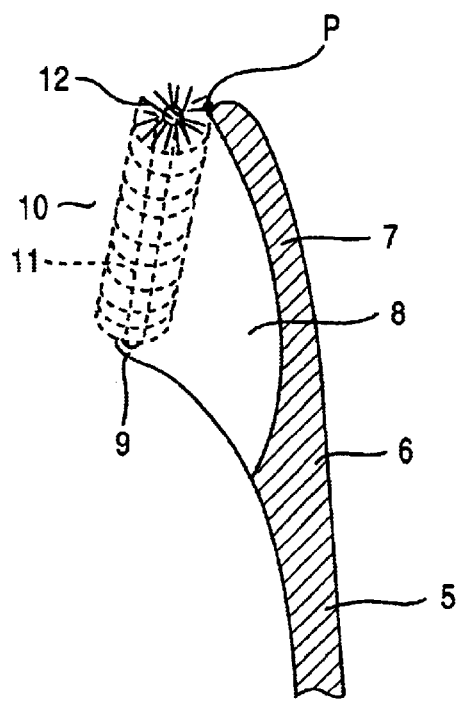
FIG. 4 illustrates enlarged section views (A, B and C) of other examples of the embodiment illustrated in FIG. 2.
Figure 4B:
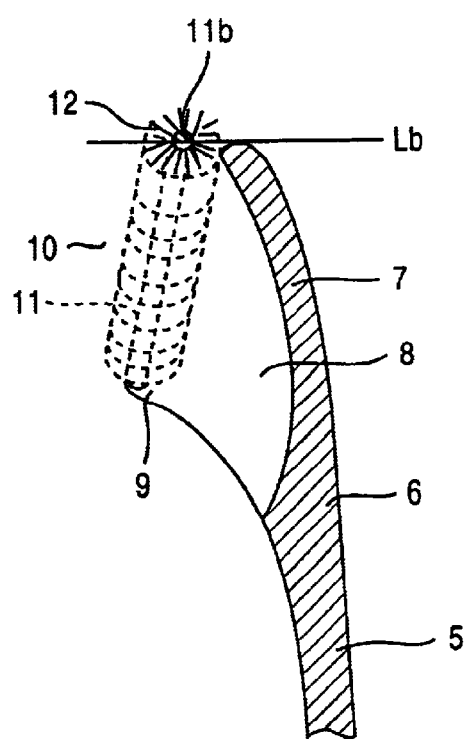
Figure 4C:
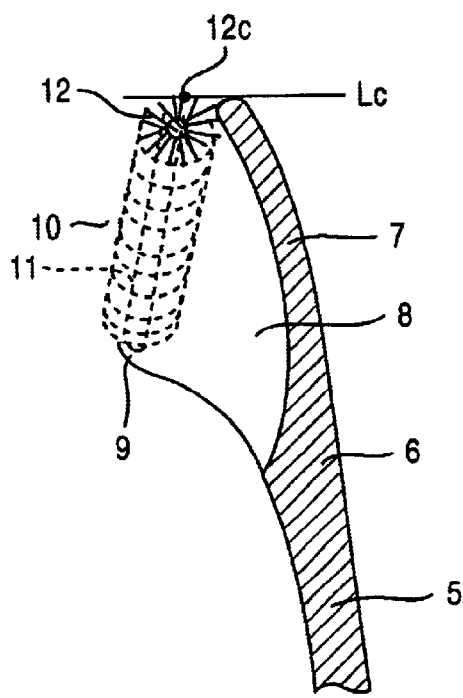
Figure 5A:
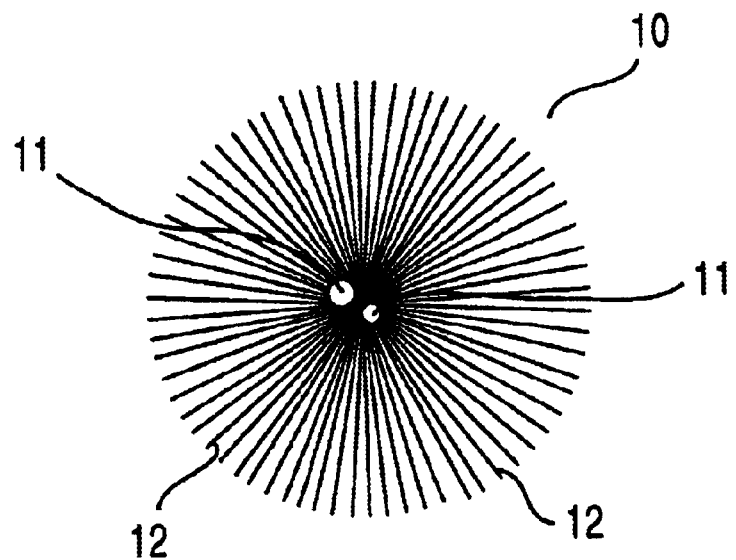
FIG. 5A shows a sectional view of the brush (10) of FIGS. 1A–4C.
Figure 5B:
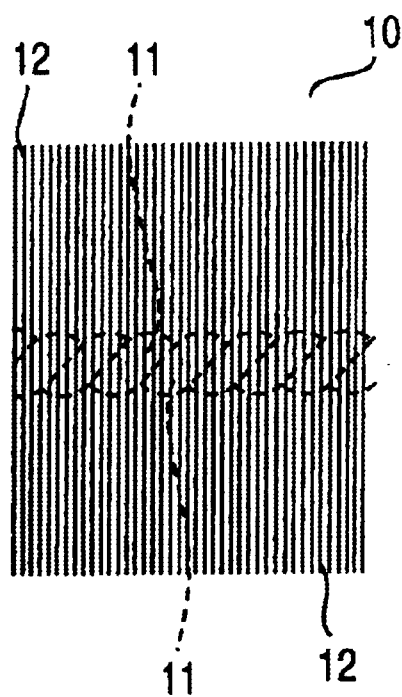
FIG. 5B shows a front view of a part of the brush (10) of FIGS. 1A–4C.

In the above-mentioned embodiment, a small gap 13 is formed between the edge of the cover 7 and the upper side of the brush 10, as illustrated in FIG. 2. The upper side of the brush 10 may be in contact with the edge of the cover 7, as illustrated in FIG. 4A. Also, the wires 11 at the tip of the brush 10 may be at the level of the tip of the cover 7, as illustrated in FIG. 4B. Further, the tip of the bristle 12 at the tip of the brush 10 may be at the level of the tip of the cover 7, as illustrated in FIG. 4C. The cover 7 should be covering the inner side of the brush 10 at least.

The present invention having the above-mentioned composition has the following effect. An outwardly curved brush 10 is attached to the head of the grip handle 1 and a spoon-shaped cover covering the inner side of the brush 10 is formed, and therefore the tongue plaque scraped from the tongue dorsum is retained inside the outwardly curved brush 10 and inside the cover 7. The scraped tongue plaque does not drop into the oral cavity and the accidental swallowing of the tongue plaque is prevented in those who need a care, such as demented aged persons or immobile aged persons.

The tongue cleaning device in the present invention comprises a spoon-shaped cover 7 formed integrally at the end of a grip handle 1 with the concave side facing below, a brush 10 for scraping the tongue plaque on the tongue dorsum formed by arranging a number of bristles 12 sprirally between two twisted wires 11, wherein said outwardly curved brush 10,is placed under said cover 7 so that said wires 11 of said brush 10 is covered by said cover 7, and both ends of the wires 11 of said brush 10 are attached to both sides of the under side of said cover 7. Therefore, the tongue plaque scraped by said brush 10 is retained in said cover 7 preventing said tongue plaque from overflowing through the upper side of said brush 10, and excessive deformation of said brush 10 due to contact pressure of said brush 10 applied onto said tongue dorsum is inhibited by said cover 7.

Furthermore, the brush is formed by arranging a number of bristles 12 spirally between the two twisted wires 11, and the elasticity of the wires 11 curved outwardly reduces the contact pressure of the brush 10 onto the tongue dorsum, preventing the injury of the lingual mucosa. Excessive deformation of the brush 10 caused by said contact pressure may reduce the scraping efficiency, but the wires 11 curved outwardly are covered by the cover 7 which serves as a stopper of the brush 10, thereby preventing excessive deformation of the brush 10 caused by said contact pressure.

By making a small gap 13 between the edge of the cover 7 and the upper side of the brush 10, the elasticity of the twisted wires is not prevented, thereby reducing said contact pressure. When the brush 10 comes in contact with the tongue dorsum, the upper end of the brush 10 comes in contact with the edge of the cover 7 and thus the scraped tongue plaque does not overflow through the upper side of the brush 7, the contact pressure of the brush 10 onto the tongue dorsum is further reduced and the foregoing various effects are accomplished.

By forming an elastic part 5 between the middle part 3 and the head 6 of the grip handle 1, three-step buffer is formed by the bristles 12 of the brush 10, the wires 11 and the elastic part 5 of the grip handle 1, and the contact pressure of the brush 10 onto the tongue dorsum is further reduced. Even if the care-taker scrapes with unconsciously strong pressure onto the tongue dorsum of those who receives the care, application of excessive contact pressure directly onto the tongue dorsum is thus prevented by the elasticity of the elastic part 5.

I claim:

1. A tongue cleaning device comprising:
   a grip handle having a head at an end;
   a brush, and
   a cover formed at the end of said grip handle covering an inner side of said brush adapted to retain the tongue plaque scraped by said brush;
   wherein:
      said brush is comprised of a spine having two ends and bristles extending perpendicularly from said spine,
      said ends of said spine are attached to opposite sides of said head, and
      said spine is bent in an arc bowing away from said handle;
   and wherein:
      said cover is integral with said end of said handle,
      an end of said cover is configured directly adjacent to and parallel to said brush, and
      said cover includes a concave side toward said brush, and a convex side away from said brush, said concave side forming a plaque-holding reservoir.

2. The tongue cleaning device of claim 1, wherein said spine of said brush is made of wire,
   further comprising a space between said brush and said cover to allow deformation of said brush toward said cover, wherein said cover is adapted to limit deformation of said brush toward said cover.

3. The tongue cleaning device of claim 2, wherein an elastic part is formed between a middle part of the grip handle and the head of the grip handle in order to reduce contact pressure onto a tongue dorsum.

4. The tongue cleaning device of claims 1 or 2, wherein a small gap is formed between the edge of the cover and the upper side of the brush.

5. The tongue cleaning device of claim 1, wherein an elastic part is formed between a middle part of the grip handle and the head of the grip handle in order to reduce contact pressure onto a tongue dorsum.

* * * * *